(12) United States Patent
Mansi et al.

(10) Patent No.: US 11,587,684 B2
(45) Date of Patent: Feb. 21, 2023

(54) PREDICTION OF TARGET ABLATION LOCATIONS FOR TREATING CARDIAC ARRHYTHMIAS USING DEEP LEARNING

(71) Applicant: Siemens Healthcare GmbH, Erlangen (DE)

(72) Inventors: Tommaso Mansi, Plainsboro, NJ (US); Tiziano Passerini, Plainsboro, NJ (US); Viorel Mihalef, North Brunswick, NJ (US)

(73) Assignee: Siemens Healthcare GmbH, Erlangen (DE)

(*) Notice: Subject to any disclaimer, the term of this patent is extended or adjusted under 35 U.S.C. 154(b) by 273 days.

(21) Appl. No.: 16/903,413

(22) Filed: Jun. 17, 2020

(65) Prior Publication Data
US 2021/0090744 A1 Mar. 25, 2021

Related U.S. Application Data

(60) Provisional application No. 62/904,844, filed on Sep. 24, 2019.

(51) Int. Cl.
| | |
|---|---|
| *G16H 50/50* | (2018.01) |
| *A61B 5/00* | (2006.01) |
| *G16H 30/40* | (2018.01) |
| *A61B 5/364* | (2021.01) |
| *G06V 10/40* | (2022.01) |

(52) U.S. Cl.
CPC .......... *G16H 50/50* (2018.01); *A61B 5/0036* (2018.08); *A61B 5/0044* (2013.01); *A61B 5/364* (2021.01); *A61B 5/4848* (2013.01); *A61B 5/7264* (2013.01); *G06V 10/40* (2022.01); *G16H 30/40* (2018.01); *A61B 2576/023* (2013.01)

(58) Field of Classification Search
CPC ........ A61B 2034/105; A61B 2034/107; A61B 2576/023; A61B 34/10; A61B 5/0036; A61B 5/0044; A61B 5/055; A61B 5/364; A61B 5/367; A61B 5/4848; A61B 5/7264; G06K 9/6271; G06V 10/40; G06V 10/454; G06V 10/82; G06V 2201/03; G16H 20/40; G16H 30/40; G16H 50/20; G16H 50/50
See application file for complete search history.

(56) References Cited

U.S. PATENT DOCUMENTS

| | | |
|---|---|---|
| 9,463,072 B2 | 10/2016 | Comaniciu et al. |
| 10,296,809 B2 | 5/2019 | Rapaka et al. |
| 10,485,510 B2 | 11/2019 | Mansi et al. |

(Continued)

OTHER PUBLICATIONS

Wellens et al., "Electrical stimulation of the heart in patients with ventricular tachycardia", Circulation, Aug. 1972, vol. 46, No. 2, pp. 216-226.

(Continued)

*Primary Examiner* — Manuchehr Rahmjoo (57) ABSTRACT

Systems and methods for generating an ablation map identifying target ablation locations on a heart of a patient are provided. One or more input medical images of a heart of a patient and a voltage map of the heart of the patient are received. An ablation map identifying target ablation locations on the heart is generated using one or more trained machine learning based models based on the one or more input medical images and the voltage map. The ablation map is output.

12 Claims, 4 Drawing Sheets

(56) References Cited

U.S. PATENT DOCUMENTS

| | | |
|---|---|---|
| 10,496,729 B2 | 12/2019 | Neumann et al. |
| 2014/0022250 A1* | 1/2014 | Mansi ..................... G06T 7/12 |
| | | 345/420 |
| 2016/0058520 A1* | 3/2016 | Yang ..................... A61B 34/10 |
| | | 703/11 |
| 2016/0196384 A1 | 7/2016 | Mansi et al. |
| 2016/0210435 A1 | 7/2016 | Neumann et al. |
| 2016/0283687 A1* | 9/2016 | Kamen ................. G16H 50/50 |

OTHER PUBLICATIONS

Baldinger et al., "Ablation of ischemic ventricular tachycardia: evidence, techniques, results, and future directions", Curr Opin Cardiol, Jan. 2016, vol. 31, No. 1, pp. 29-36.

Prakosa, Adityo, et al. "Personalized virtual-heart technology for guiding the ablation of infarct-related ventricular tachycardia." Nature biomedical engineering 2.10 (2018): 732.

Ashikaga, Hiroshi, et al. "Feasibility of image-based simulation to estimate ablation target in human ventricular arrhythmia." Heart rhythm 10.8 (2013): 1109-1116.

* cited by examiner

100

```
┌─────────────────────────────────────────────────────────────┐
│ Receive one or more input medical images of a heart of a   │
│ patient and a voltage map of the heart of the patient      │
│                         102                                 │
└─────────────────────────────────────────────────────────────┘
                              │
                              ▼
┌─────────────────────────────────────────────────────────────┐
│ Generate an ablation map identifying target ablation        │
│ locations on the heart using one or more trained machine    │
│ learning based networks based on the one or more input     │
│ medical images and the voltage map                          │
│                         104                                 │
└─────────────────────────────────────────────────────────────┘
                              │
                              ▼
┌─────────────────────────────────────────────────────────────┐
│                 Output the ablation map                     │
│                         106                                 │
└─────────────────────────────────────────────────────────────┘
```

PREDICTION OF TARGET ABLATION LOCATIONS FOR TREATING CARDIAC ARRHYTHMIAS USING DEEP LEARNING

CROSS-REFERENCE TO RELATED APPLICATIONS

This application claims the benefit of U.S. Provisional Application No. 62/904,844, filed Sep. 24, 2019, the disclosure of which is incorporated herein by reference in its entirety.

TECHNICAL FIELD

The present invention relates generally to the prediction of target ablation locations for treating cardiac arrhythmias, and in particular to the prediction of target ablation locations on a heart of a patient for treating cardiac arrhythmias using deep learning.

BACKGROUND

Cardiac arrhythmia is a condition in which the heart rate of a patient is irregular. Cardiac arrhythmia is typically treated by catheter ablation. In the current clinical practice, target ablation locations are typically identified using electro-anatomical maps. However, such electro-anatomical maps are acquired invasively using electrophysiology systems. Additionally, in the case of persistent or permanent atrial fibrillation and ventricular tachycardia, low conductivity areas within fibrosis tissue or around scar tissue are difficult to identify from electro-anatomical maps. Imaging, such as, e.g., DE-MRI (delayed enhancement magnetic resonance imaging), CT (computed tomography) scans, and ultrasound ICE (intra-cardiac echo), has been introduced to provide additional information for identifying target locations for ablation. However, the sensitivity of localization resulting from such imaging is sub-optimal.

Recently, computational models have been proposed to assess whether specific fibrosis or scar tissue is arrhythmogenic based on imaging data. The objective is to combine imaging data with a patient-specific computational model of cardiac electrophysiology to simulate arrhythmias of the patient and identify ablation targets by studying the electrical activation or by performing virtual ablations. However, such computational models are sensitive to model parameters (e.g., conduction velocity and action potential duration), largely depend on scar/fibrosis segmentation, and are computationally demanding. Further, such computational modeling is performed prior to an intervention, and therefore real-time data acquired during the intervention cannot be leveraged.

BRIEF SUMMARY OF THE INVENTION

In accordance with one or more embodiments, systems and methods for generating an ablation map identifying target ablation locations on the heart of a patient are provided. One or more input medical images of a heart of a patient and a voltage map of the heart of the patient are received. An ablation map identifying target ablation locations on the heart is generated using one or more trained machine learning based models based on the one or more input medical images and the voltage map. The ablation map is output.

In one embodiment, features are extracted from the voltage map using an encoder network and the ablation map is generated based on the features extracted from the voltage map.

In one embodiment, an activation map of the heart of the patient is received and the ablation map is generated based on the activation map. In one embodiment, features are extracted from the activation map and the ablation map is generated based on the features extracted from the activation map.

In one embodiment, the voltage map is generated by simulating cardiac electrophysiology of the patient using a patient-specific model of the heart.

In one embodiment, the one or more trained machine learning based models are trained using a synthetic training dataset. The synthetic training dataset is generated by creating a fiber architecture for each of one or more anatomical models, generating a generating a set of electrical tissue properties for each of the one or more anatomical models, simulating cardiac electrophysiology over a period of time for a number of stimulations, and identifying target ablation locations based on the simulating to generate a training ablation map.

In one embodiment, the ablation map is generated based on a dose of a drug the patient is on or motion of the patient in a pair of the plurality of input medical images.

In one embodiment, ablation is performed on the target ablation locations identified in the ablation map.

These and other advantages of the invention will be apparent to those of ordinary skill in the art by reference to the following detailed description and the accompanying drawings.

DETAILED DESCRIPTION

The present invention generally relates to methods and systems for predicting target ablation locations for treating cardiac arrhythmias using deep learning. Embodiments of the present invention are described herein to give a visual understanding of such methods and systems. A digital image is often composed of digital representations of one or more objects (or shapes). The digital representation of an object is often described herein in terms of identifying and manipulating the objects. Such manipulations are virtual manipulations accomplished in the memory or other circuitry/hardware of a computer system. Accordingly, is to be understood that embodiments of the present invention may be performed within a computer system using data stored within the computer system.

Embodiments described herein provide for the generation of an ablation map identifying target ablation locations on the heart of a patient for treating cardiac arrhythmias. The target ablation locations represent locations on the heart of the patient at which ablation is performed to scar or destroy tissue. A trained deep image-to-image network receives an input medical image of the heart of the patient, a voltage map of the heart of the patient, and an activation map of the heart of the patient and outputs the ablation map. Advantageously, embodiments described herein utilize a trained deep image-to-image network to identify target ablation locations, thereby avoiding computationally expensive computational models, and their inherent uncertainty, used in conventional approaches. Embodiments described herein identify the minimal number of target ablation locations that is effective for treating cardiac arrhythmias, thereby improving patient outcome and minimizing costly and dangerous re-performance of ablation.

It should be understood that while embodiments described herein are described with respect to identifying target ablation locations on the heart of a patient for treating cardiac arrhythmias, embodiments described herein are not so limited. Embodiments described herein may be applied to identify any target location on the heart of the patient for treating any cardiac disease. In one example, embodiments described herein may be applied to guide to a selection of a form of ablation (e.g., radiofrequency ablation, cryoablation, pharmacological ablation, etc.).

Figure 1:
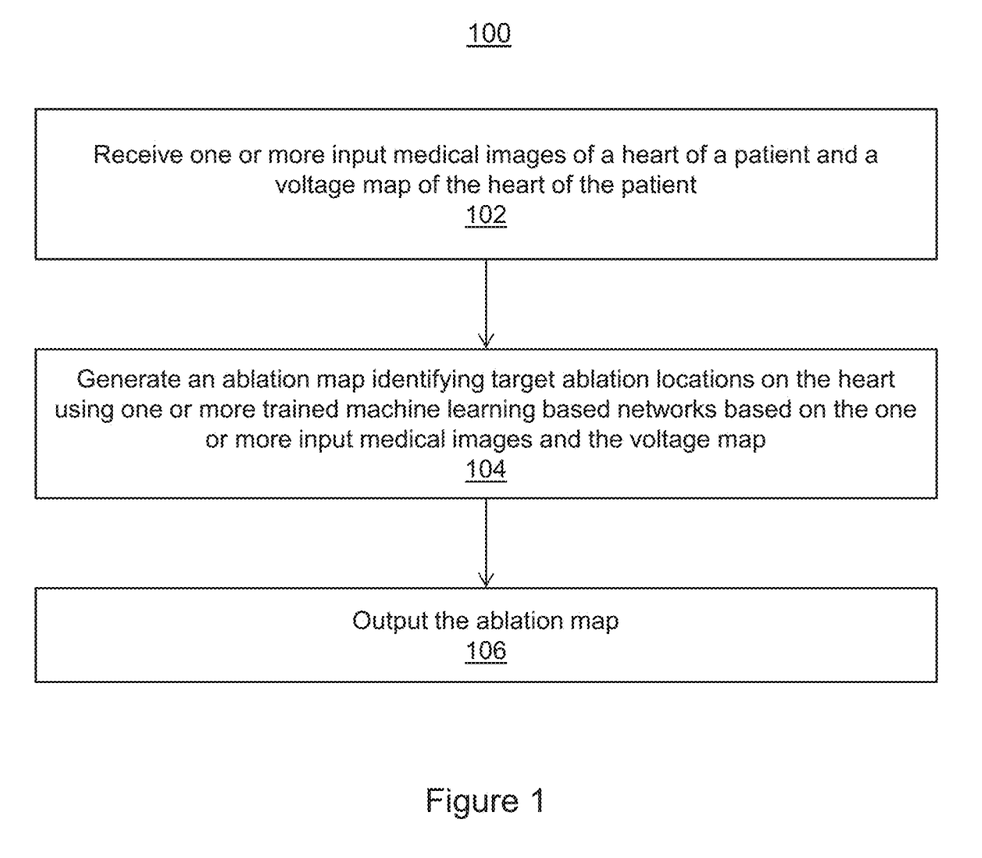
FIG. 1 shows a method for generating an ablation map identifying target ablation locations on a heart of a patient for treating cardiac arrhythmias, in accordance with one or more embodiments.

FIG. 1 shows a method 100 for generating an ablation map identifying target ablation locations on a heart of a patient for treating cardiac arrhythmias, in accordance with one or more embodiments. The steps of method 100 may be performed by one or more suitable computing devices, such as, e.g., computer 402 of FIG. 4. In one embodiment, the computing device performing the steps of method 100 may be integrated within an interventional system, such as, e.g., a C-arm, an interventional MRI (magnetic resonance imaging) scanner, or an ultrasound ICE (intra-cardiac echo)) scanner. The interventional system may display the ablation map in substantially real time or near real time during the interventional procedure based on data (e.g., medical images, voltage maps, activation maps) acquired during the interventional procedure.

At step 102, one or more input medical images of a heart of a patient and a voltage map of the heart of the patient are received. In one embodiment, an activation map of the heart is also received.

In one embodiment, the input medical images are DE-MRI (delayed enhancement MRI) images, cine-MRI images, CT (computed tomography) images, or ultrasound ICE images. However, the input medical images may be of any other suitable modality, such as, e.g., MRI, x-ray, ultrasound, or any other modality or combination of modalities. The input medical images may comprise 2D images or 3D volumes, and may comprise a single image or a plurality of images (e.g., a sequence of images acquired over time). The input medical images may be received directly from an image acquisition device, such as, e.g., a CT, MRI, or ultrasound scanner, as the input medical images are acquired, or can be received by loading previously acquired input medical images from a storage or memory of a computer system or receiving the input medical images from a remote computer system.

The voltage map of the heart of the patient represents the electrical activity over the surface of the heart. The activation map of the heart of the patient represents activation time patterns over the surface of the heart. In one embodiment, the voltage map and/or the activation map are a virtual voltage map and/or a virtual activation map, respectively, generated by simulating the heart of the patient using a patient-specific physiological model of the heart. In another embodiment, the voltage map and/or the activation map are manually generated by a clinician using invasive electrophysiological systems.

At step 104, an ablation map identifying target ablation locations on the heart is generated using one or more trained machine learning based models based on the one or more input medical images and the voltage map. In one embodiment, the ablation map is generated further based on the activation map. In one embodiment, the trained machine learning based models include a deep image-to-image network. The deep image-to-image network is trained to map the input medical images, the voltage map, and the activation map to the ablation map. The deep image-to-image network is trained during a prior offline or training stage. During the training stage, parameters of the deep image-to-image network are optimized using a training dataset such that the predicted ablation map matches ground truth values of the training dataset. The problem is therefore modelled as a detection problem. Once trained, the deep image-to-image network is applied at step 104 during an online or inference stage to generate an ablation map.

In one embodiment, the training dataset used for training the deep image-to-image network comprises a synthetic training dataset generated using a computational model of cardiac electrophysiology. The computational model of cardiac electrophysiology is generated based on anatomical models. In one embodiment, the anatomical models are created from a database of K medical images (e.g., DE-MRI or cine-MRI images, CT images, or ultrasound ICE images) by segmenting the cardiac chambers, myocardial scarring, and cardiac fibrosis, e.g., using machine learning based segmentation techniques. In another embodiment, the anatomical models are synthetically generated based on atlases and population-based models.

A fiber architecture is then created for each anatomical model using, e.g., a rule-based model, an atlas, or patient-specific data (e.g., diffusion-tensor imaging). For each anatomical model, N sets of electrical tissue properties are generated to generate the computational model of cardiac electrophysiology. The N sets of electrical tissue properties may be estimated from available clinical data, as described in U.S. Pat. No. 10,296,809, the disclosure of which is incorporated herein by reference in its entirety. In one embodiment, population average values reported in literature may be varied randomly within ranges corresponding to normal or pathological conditions.

Cardiac electrophysiology is simulated over a period of time at sinus rhythm for the N sets of electrical tissue properties for a number M of programmed stimulations. The M programmed stimulations refer to the clinical practice of pacing the heart with a pattern of repeated electrical stimuli to induce tachycardia. Inducing tachycardia will allow the user to 'see' the source of the arrhythmia and therefore ablate it. The M programmed stimulation can be selected from a library of programmed stimulations commonly used in clinical practice. In one embodiment, different models may be trained for generating the ablation map, each for a different selection of the M programmed stimulation. The selection allows a trade-off between time/cost needed to generate the training set (the larger the M programmed stimulation, the more time is required to generate the samples) and the training set comprising enough examples of potentially arrhythmogenic conditions, so that the ablation map is defined more robustly.

Target ablation locations are then identified from the simulations to generate a training ablation map A that identifies a minimal set of ablations that stop the arrhythmia for all M programmed stimulation. In one embodiment, the target ablation locations are identified by identifying simulations for which the programmed stimulation generated arrhythmia. One of a plurality of predetermined candidate ablation maps are applied for each identified simulation and the simulation is repeated. This process may be repeated for any number of iterations (e.g., for each candidate ablation map). A final ablation map is selected as the candidate ablation map comprising the least amount of ablated tissue that prevents the arrhythmia from manifesting in all simulations in which it was initially observed. The predetermined candidate ablation maps may be generated using any suitable approach. In one embodiment, the predetermined candidate ablation maps are generated systematically, e.g., by incrementally adding simulated ablation lesions as if simulating an actual ablation procedure.

The ablation map, the medical images, the virtual voltage map, and the virtual activation map are output as part of the synthetic training dataset. In one embodiment, the synthetic training dataset is complemented with a patient-specific training dataset for training the deep image-to-image network, where the voltage map, the activation map, and the ablation map of the patient-specific training data are acquired during the procedure using invasive mapping systems. Computational models of cardiac electrophysiology are further described in U.S. Pat. No. 9,463,072, issued Oct. 11, 2016, and U.S. Pat. No. 10,485,510, issued Nov. 26, 2019, the disclosures of which are incorporated herein by reference in their entirety.

In one embodiment, instead of directly inputting the voltage map and/or the activation map into the deep image-to-image network to generate the ablation map, features are extracted from the voltage map and/or the activation map and the extracted features of the voltage map and/or the activation map are input into the deep image-to-image network to generate the ablation map. Preprocessing the electro-anatomical signals in the voltage map and/or the activation map will simplify the task of the deep image-to-image network. Images (e.g., the voltage map and/or the activation map) and non-images (e.g., the extracted features) may be processed by two different networks (e.g., convolutional neural network for images and a fully convolutional network for non-images) and the respective outputs may be concatenated before the final layer of the deep image-to-image network. The output of the fully convolutional network may also be concatenated to the encoded features of the deep image-to-image network. The fully convolutional network may be in the form of an encoding network for encoding the voltage map and/or activation map into low dimensional features. Because arrhythmias are dynamic features and their location may vary based on the electrical function (e.g., entrance and exits of a channel, may vary depending on the direction of the electrical wave), features extracted from the voltage map and/or the activation map would be helpful in generating the ablation map. The encoding network is trained, together with a decoding network, during a prior training stage. The encoding network and the decoding network together form an autoencoder network. During the training stage, the encoding network encodes training voltage maps into features and the decoding network reconstructs the training voltage maps from the encoded features. Once trained, the encoding network may be applied during the inference stage at step 104. The decoding network is only utilized during the training stage, and is not applied during the inference stage. The deep image-to-image network and the encoder/decoder network may be individually trained, or trained together in an end-to-end manner.

In one embodiment, the ablation map may be generated further based on additional electrical signals of the patient inputted into the machine learning based models, such as, e.g., body surface maps or electrocardiograms (e.g., 12 lead electrocardiograms). In one embodiment, the ablation map may be generated further based on the effect of drugs the patient is on. For instance, the dose of the drugs may be input into the machine learning based models, while the machine learning based models learn the effects of the drugs at the dose based on the training dataset. In one embodiment, the ablation map may be generated further based on motion of the patient in the input medical images. For instance, functional features may be extracted from a pair of input medical images by inputting the pair of input medical images into an encoder network.

In one embodiment, the ablation map may be generated using the machine learning based models without using the voltage map and/or the activation map.

At step 106, the ablation map is output. The ablation map identifying a minimal number of target ablation location to effectively treat cardiac arrhythmia, thereby improving patient outcome and minimizing the cost and risk or having to re-perform an ablation procedure. The ablation map can be output by displaying the ablation map on a display device of a computer system, storing the ablation map on a memory or storage of a computer system, or by transmitting the ablation map to a remote computer system.

In one embodiment, ablation of the heart of the patient is performed at the target ablation locations identified in the ablation map. In one embodiment, the ablation map may be output to a robotic system to guide an ablation catheter of the robotic system directly to the target ablation locations. In one embodiment, the target ablation locations identified in the ablation map may be co-registered to a therapy system using 2D/3D registration methods (e.g., for a C-arm) or directly in an iCMR (interventional cardiovascular magnetic resonance) imaging setup (e.g., for real-time guidance). In one embodiment, by modelling the ablation as a scar or by directly mapping a lesion observed in interventional images (e.g., ultrasound ICE, iCMR), the machine learning based networks may be applied recursively to guide repeated ablations during the procedure.

Advantageously, embodiments described herein utilize a large training database and one or more machine learning based models or networks such that the machine learning based networks capture subtle features that identify target ablation locations with improved sensitivity and specificity, which could not be identified using conventional computational models due to the noise in the data. Further, such machine learning based networks are significantly more computationally efficient than conventional computational models and, as a result, the machine learning based networks may be applied during planning of the ablation procedure or during the ablation procedure (e.g., for guidance). In addition, such machine learning based networks may be implemented on low cost computing hardware, making the machine learning based networks more cost efficient to implement compared to conventional computational models.

Embodiments described herein are described with respect to the claimed systems as well as with respect to the claimed methods. Features, advantages or alternative embodiments herein can be assigned to the other claimed objects and vice versa. In other words, claims for the systems can be improved with features described or claimed in the context of the methods. In this case, the functional features of the method are embodied by objective units of the providing system.

Furthermore, embodiments described herein are described with respect to methods and systems for generating an ablation map identifying target ablation locations on a heart of a patient using trained machine learning based networks, as well as with respect to methods and systems for training machine learning based networks for generating an ablation map identifying target ablation locations on a heart of a patient. Features, advantages or alternative embodiments herein can be assigned to the other claimed objects and vice versa. In other words, claims for methods and systems for training machine learning based networks can be improved with features described or claimed in context of the methods and systems for utilizing trained machine learning based networks, and vice versa.

In particular, the trained machine learning based networks of the methods and systems for generating an ablation map identifying target ablation locations on a heart of a patient can be adapted by the methods and systems for training the machine learning based networks for generating an ablation map identifying target ablation locations on a heart of a patient. Furthermore, the input data of the trained machine learning based network can comprise advantageous features and embodiments of the training input data, and vice versa. Furthermore, the output data of the trained machine learning based network can comprise advantageous features and embodiments of the output training data, and vice versa.

In general, a trained machine learning based network mimics cognitive functions that humans associate with other human minds. In particular, by training based on training data, the trained machine learning based network is able to adapt to new circumstances and to detect and extrapolate patterns.

In general, parameters of a machine learning based network can be adapted by means of training. In particular, supervised training, semi-supervised training, unsupervised training, reinforcement learning and/or active learning can be used. Furthermore, representation learning (an alternative term is "feature learning") can be used. In particular, the parameters of the trained machine learning based network can be adapted iteratively by several steps of training.

In particular, a trained machine learning based network can comprise a neural network, a support vector machine, a decision tree, and/or a Bayesian network, and/or the trained machine learning based network can be based on k-means clustering, Q-learning, genetic algorithms, and/or association rules. In particular, a neural network can be a deep neural network, a convolutional neural network, or a convolutional deep neural network. Furthermore, a neural network can be an adversarial network, a deep adversarial network and/or a generative adversarial network.

Figure 2:
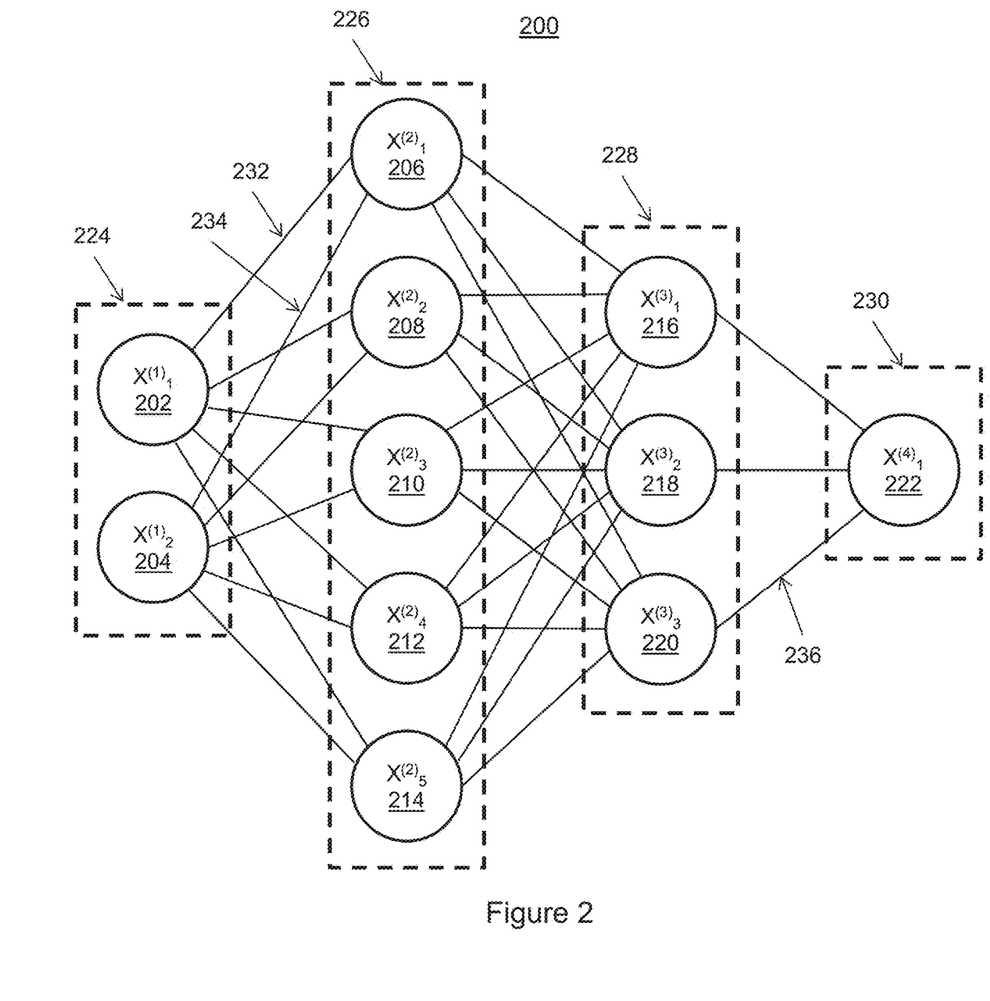
FIG. 2 shows an exemplary artificial neural network that may be used to implement one or more embodiments described herein.

FIG. 2 shows an embodiment of an artificial neural network 200, in accordance with one or more embodiments. Alternative terms for "artificial neural network" are "neural network", "artificial neural net" or "neural net". Machine learning networks described herein, such as, e.g., the machine learning based networks (including the deep image-to-image network and the encoder and decoder networks) applied at step 104 of FIG. 1, may be implemented using artificial neural network 200.

The artificial neural network 200 comprises nodes 202-222 and edges 232, 234, . . . , 236, wherein each edge 232, 234, . . . , 236 is a directed connection from a first node 202-222 to a second node 202-222. In general, the first node 202-222 and the second node 202-222 are different nodes 202-222, it is also possible that the first node 202-222 and the second node 202-222 are identical. For example, in FIG. 2, the edge 232 is a directed connection from the node 202 to the node 206, and the edge 234 is a directed connection from the node 204 to the node 206. An edge 232, 234, . . . , 236 from a first node 202-222 to a second node 202-222 is also denoted as "ingoing edge" for the second node 202-222 and as "outgoing edge" for the first node 202-222.

In this embodiment, the nodes 202-222 of the artificial neural network 200 can be arranged in layers 224-230, wherein the layers can comprise an intrinsic order introduced by the edges 232, 234, . . . , 236 between the nodes 202-222. In particular, edges 232, 234, . . . , 236 can exist only between neighboring layers of nodes. In the embodiment shown in FIG. 2, there is an input layer 224 comprising only nodes 202 and 204 without an incoming edge, an output layer 230 comprising only node 222 without outgoing edges, and hidden layers 226, 228 in-between the input layer 224 and the output layer 230. In general, the number of hidden layers 226, 228 can be chosen arbitrarily. The number of nodes 202 and 204 within the input layer 224 usually relates to the number of input values of the neural network 200, and the number of nodes 222 within the output layer 230 usually relates to the number of output values of the neural network 200.

In particular, a (real) number can be assigned as a value to every node 202-222 of the neural network 200. Here, $x^{(n)}_i$ denotes the value of the i-th node 202-222 of the n-th layer 224-230. The values of the nodes 202-222 of the input layer 224 are equivalent to the input values of the neural network 200, the value of the node 222 of the output layer 230 is equivalent to the output value of the neural network 200. Furthermore, each edge 232, 234, . . . , 236 can comprise a weight being a real number, in particular, the weight is a real number within the interval [−1, 1] or within the interval [0, 1]. Here, $w^{(m,n)}_{i,j}$ denotes the weight of the edge between the i-th node 202-222 of the m-th layer 224-230 and the j-th node 202-222 of the n-th layer 224-230. Furthermore, the abbreviation $w^{(n)}_{i,j}$ is defined for the weight $w^{(n,n+1)}_{i,j}$.

In particular, to calculate the output values of the neural network 200, the input values are propagated through the neural network. In particular, the values of the nodes 202-222 of the (n+1)-th layer 224-230 can be calculated based on the values of the nodes 202-222 of the n-th layer 224-230 by $$x_j^{(n+1)} = f(\Sigma_i x_i^{(n)} \cdot w_{i,j}^{(n)}).$$

Herein, the function f is a transfer function (another term is "activation function"). Known transfer functions are step functions, sigmoid function (e.g. the logistic function, the generalized logistic function, the hyperbolic tangent, the Arctangent function, the error function, the smoothstep function) or rectifier functions The transfer function is mainly used for normalization purposes.

In particular, the values are propagated layer-wise through the neural network, wherein values of the input layer 224 are given by the input of the neural network 200, wherein values of the first hidden layer 226 can be calculated based on the values of the input layer 224 of the neural network, wherein values of the second hidden layer 228 can be calculated based in the values of the first hidden layer 226, etc.

In order to set the values $w^{(m,n)}_{i,j}$ for the edges, the neural network 200 has to be trained using training data. In particular, training data comprises training input data and training output data (denoted as $t_i$). For a training step, the neural network 200 is applied to the training input data to generate calculated output data. In particular, the training data and the calculated output data comprise a number of values, said number being equal with the number of nodes of the output layer.

In particular, a comparison between the calculated output data and the training data is used to recursively adapt the weights within the neural network 200 (backpropagation algorithm). In particular, the weights are changed according to $$w'_{i,j}{}^{(n)} = w_{i,j}{}^{(n)} - \gamma \cdot \delta_j{}^{(n)} \cdot x_i{}^{(n)}$$

wherein $\gamma$ is a learning rate, and the numbers $\delta^{(n)}{}_j$ can be recursively calculated as $$\delta_j{}^{(n)} = (\Sigma_k \delta_k{}^{(n+1)} \cdot w_{j,k}{}^{(n+1)}) \cdot f'(\Sigma_i x_i{}^{(n)} \cdot w_{i,j}{}^{(n)})$$

based on $\delta^{(n+1)}{}_j$, if the (n+1)-th layer is not the output layer, and $$\delta_j{}^{(n)} = (x_k{}^{(n+1)} - t_j{}^{(n+1)}) \cdot f'(\Sigma_i x_i{}^{(n)} \cdot w_{i,j}{}^{(n)})$$

if the (n+1)-th layer is the output layer 230, wherein f' is the first derivative of the activation function, and $y^{(n+1)}{}_j$ is the comparison training value for the j-th node of the output layer 230.

Figure 3:
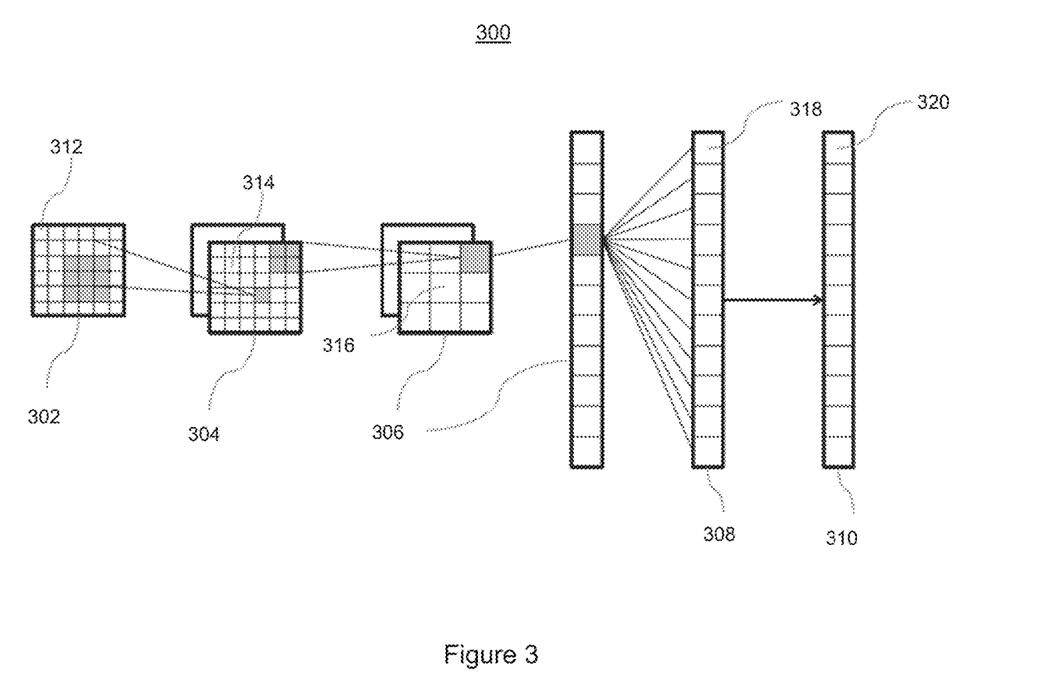
FIG. 3 shows a convolutional neural network that may be used to implement one or more embodiments described herein.

FIG. 3 shows a convolutional neural network 300, in accordance with one or more embodiments. Machine learning networks described herein, such as, e.g., the machine learning based networks (including the deep image-to-image network and the encoder and decoder networks) applied at step 104 of FIG. 1, may be implemented using convolutional neural network 300.

In the embodiment shown in FIG. 3, the convolutional neural network comprises 300 an input layer 302, a convolutional layer 304, a pooling layer 306, a fully connected layer 308, and an output layer 310. Alternatively, the convolutional neural network 300 can comprise several convolutional layers 304, several pooling layers 306, and several fully connected layers 308, as well as other types of layers. The order of the layers can be chosen arbitrarily, usually fully connected layers 308 are used as the last layers before the output layer 310.

In particular, within a convolutional neural network 300, the nodes 312-320 of one layer 302-310 can be considered to be arranged as a d-dimensional matrix or as a d-dimensional image. In particular, in the two-dimensional case the value of the node 312-320 indexed with i and j in the n-th layer 302-310 can be denoted as $x^{(n)}{}_{[i,j]}$. However, the arrangement of the nodes 312-320 of one layer 302-310 does not have an effect on the calculations executed within the convolutional neural network 300 as such, since these are given solely by the structure and the weights of the edges.

In particular, a convolutional layer 304 is characterized by the structure and the weights of the incoming edges forming a convolution operation based on a certain number of kernels. In particular, the structure and the weights of the incoming edges are chosen such that the values $x^{(n)}{}_k$ of the nodes 314 of the convolutional layer 304 are calculated as a convolution $x^{(n)}{}_k = K_k * x^{(n-1)}$ based on the values $x^{(n-1)}$ of the nodes 312 of the preceding layer 302, where the convolution * is defined in the two-dimensional case as $$x_k{}^{(n)}[i,j] = (K_k * x^{(n-1)})[i,j] = \Sigma_{i'} \Sigma_{j'} K_k[i',j'] \cdot x^{(n-1)}[i-i',j-j'].$$

Here the k-th kernel $K_k$ is a d-dimensional matrix (in this embodiment a two-dimensional matrix), which is usually small compared to the number of nodes 312-318 (e.g. a 3×3 matrix, or a 5×5 matrix). In particular, this implies that the weights of the incoming edges are not independent, but chosen such that they produce said convolution equation. In particular, for a kernel being a 3×3 matrix, there are only 9 independent weights (each entry of the kernel matrix corresponding to one independent weight), irrespectively of the number of nodes 312-320 in the respective layer 302-310. In particular, for a convolutional layer 304, the number of nodes 314 in the convolutional layer is equivalent to the number of nodes 312 in the preceding layer 302 multiplied with the number of kernels.

If the nodes 312 of the preceding layer 302 are arranged as a d-dimensional matrix, using a plurality of kernels can be interpreted as adding a further dimension (denoted as "depth" dimension), so that the nodes 314 of the convolutional layer 314 are arranged as a (d+1)—dimensional matrix. If the nodes 312 of the preceding layer 302 are already arranged as a (d+1)—dimensional matrix comprising a depth dimension, using a plurality of kernels can be interpreted as expanding along the depth dimension, so that the nodes 314 of the convolutional layer 304 are arranged also as a (d+1)—dimensional matrix, wherein the size of the (d+1)—dimensional matrix with respect to the depth dimension is by a factor of the number of kernels larger than in the preceding layer 302.

The advantage of using convolutional layers 304 is that spatially local correlation of the input data can be exploited by enforcing a local connectivity pattern between nodes of adjacent layers, in particular by each node being connected to only a small region of the nodes of the preceding layer.

In embodiment shown in FIG. 3, the input layer 302 comprises 36 nodes 312, arranged as a two-dimensional 6×6 matrix. The convolutional layer 304 comprises 72 nodes 314, arranged as two two-dimensional 6×6 matrices, each of the two matrices being the result of a convolution of the values of the input layer with a kernel. Equivalently, the nodes 314 of the convolutional layer 304 can be interpreted as arranges as a three-dimensional 6×6×2 matrix, wherein the last dimension is the depth dimension.

A pooling layer 306 can be characterized by the structure and the weights of the incoming edges and the activation function of its nodes 316 forming a pooling operation based on a non-linear pooling function f. For example, in the two dimensional case the values $x^{(n)}$ of the nodes 316 of the pooling layer 306 can be calculated based on the values $x^{(n-1)}$ of the nodes 314 of the preceding layer 304 as $$x^{(n)}[i,j] = f(x^{(n-1)}[id_1, jd_2], \ldots, x^{(n-1)}[id_1 + d_1 - 1, jd_2 + d_2 - 1])$$

In other words, by using a pooling layer 306, the number of nodes 314, 316 can be reduced, by replacing a number d1·d2 of neighboring nodes 314 in the preceding layer 304 with a single node 316 being calculated as a function of the values of said number of neighboring nodes in the pooling layer. In particular, the pooling function f can be the max-function, the average or the L2-Norm. In particular, for a pooling layer 306 the weights of the incoming edges are fixed and are not modified by training.

The advantage of using a pooling layer 306 is that the number of nodes 314, 316 and the number of parameters is reduced. This leads to the amount of computation in the network being reduced and to a control of overfitting.

In the embodiment shown in FIG. 3, the pooling layer 306 is a max-pooling, replacing four neighboring nodes with only one node, the value being the maximum of the values of the four neighboring nodes. The max-pooling is applied to each d-dimensional matrix of the previous layer; in this embodiment, the max-pooling is applied to each of the two two-dimensional matrices, reducing the number of nodes from 72 to 18.

A fully-connected layer 308 can be characterized by the fact that a majority, in particular, all edges between nodes 316 of the previous layer 306 and the nodes 318 of the fully-connected layer 308 are present, and wherein the weight of each of the edges can be adjusted individually.

In this embodiment, the nodes 316 of the preceding layer 306 of the fully-connected layer 308 are displayed both as two-dimensional matrices, and additionally as non-related nodes (indicated as a line of nodes, wherein the number of nodes was reduced for a better presentability). In this embodiment, the number of nodes 318 in the fully connected layer 308 is equal to the number of nodes 316 in the preceding layer 306. Alternatively, the number of nodes 316, 318 can differ.

Furthermore, in this embodiment, the values of the nodes 320 of the output layer 310 are determined by applying the Softmax function onto the values of the nodes 318 of the preceding layer 308. By applying the Softmax function, the sum the values of all nodes 320 of the output layer 310 is 1, and all values of all nodes 320 of the output layer are real numbers between 0 and 1.

A convolutional neural network 300 can also comprise a ReLU (rectified linear units) layer. In particular, the number of nodes and the structure of the nodes contained in a ReLU layer is equivalent to the number of nodes and the structure of the nodes contained in the preceding layer. In particular, the value of each node in the ReLU layer is calculated by applying a rectifying function to the value of the corresponding node of the preceding layer. Examples for rectifying functions are $f(x)=\max(0,x)$, the tangent hyperbolics function or the sigmoid function.

In particular, convolutional neural networks 300 can be trained based on the backpropagation algorithm. For preventing overfitting, methods of regularization can be used, e.g. dropout of nodes 312-320, stochastic pooling, use of artificial data, weight decay based on the L1 or the L2 norm, or max norm constraints.

Systems, apparatuses, and methods described herein may be implemented using digital circuitry, or using one or more computers using well-known computer processors, memory units, storage devices, computer software, and other components. Typically, a computer includes a processor for executing instructions and one or more memories for storing instructions and data. A computer may also include, or be coupled to, one or more mass storage devices, such as one or more magnetic disks, internal hard disks and removable disks, magneto-optical disks, optical disks, etc.

Systems, apparatus, and methods described herein may be implemented using computers operating in a client-server relationship. Typically, in such a system, the client computers are located remotely from the server computer and interact via a network. The client-server relationship may be defined and controlled by computer programs running on the respective client and server computers.

Systems, apparatus, and methods described herein may be implemented within a network-based cloud computing system. In such a network-based cloud computing system, a server or another processor that is connected to a network communicates with one or more client computers via a network. A client computer may communicate with the server via a network browser application residing and operating on the client computer, for example. A client computer may store data on the server and access the data via the network. A client computer may transmit requests for data, or requests for online services, to the server via the network. The server may perform requested services and provide data to the client computer(s). The server may also transmit data adapted to cause a client computer to perform a specified function, e.g., to perform a calculation, to display specified data on a screen, etc. For example, the server may transmit a request adapted to cause a client computer to perform one or more of the steps or functions of the methods and workflows described herein, including one or more of the steps or functions of FIG. 1. Certain steps or functions of the methods and workflows described herein, including one or more of the steps or functions of FIG. 1, may be performed by a server or by another processor in a network-based cloud-computing system. Certain steps or functions of the methods and workflows described herein, including one or more of the steps of FIG. 1, may be performed by a client computer in a network-based cloud computing system. The steps or functions of the methods and workflows described herein, including one or more of the steps of FIG. 1, may be performed by a server and/or by a client computer in a network-based cloud computing system, in any combination.

Systems, apparatus, and methods described herein may be implemented using a computer program product tangibly embodied in an information carrier, e.g., in a non-transitory machine-readable storage device, for execution by a programmable processor; and the method and workflow steps described herein, including one or more of the steps or functions of FIG. 1, may be implemented using one or more computer programs that are executable by such a processor. A computer program is a set of computer program instructions that can be used, directly or indirectly, in a computer to perform a certain activity or bring about a certain result. A computer program can be written in any form of programming language, including compiled or interpreted languages, and it can be deployed in any form, including as a stand-alone program or as a module, component, subroutine, or other unit suitable for use in a computing environment.

Figure 4:
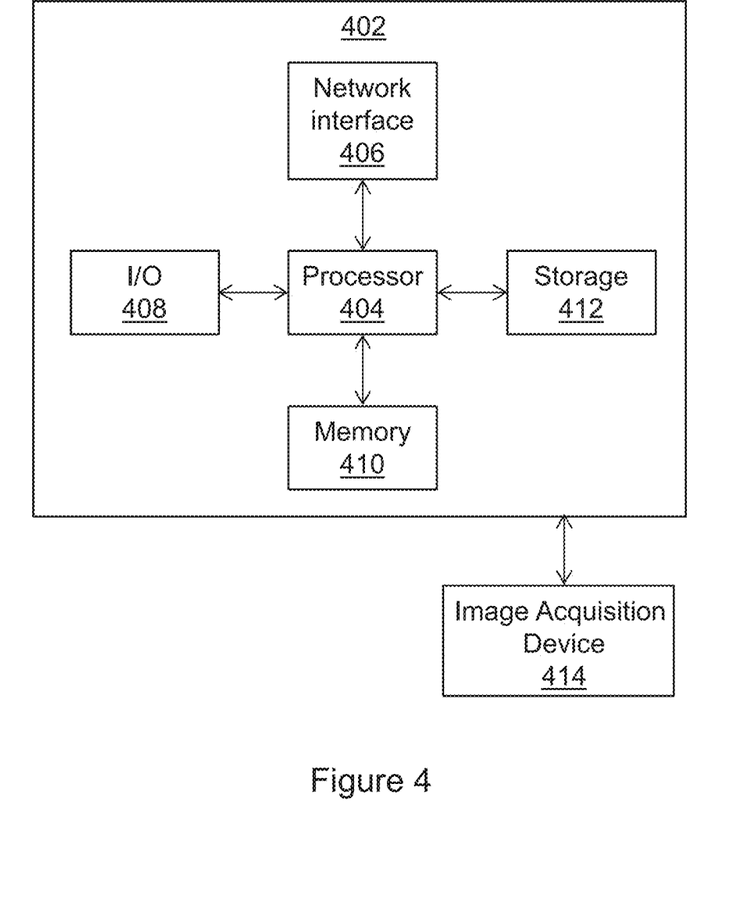
FIG. 4 shows a high-level block diagram of a computer that may be used to implement one or more embodiments described herein.

A high-level block diagram of an example computer 402 that may be used to implement systems, apparatus, and methods described herein is depicted in FIG. 4. Computer 402 includes a processor 404 operatively coupled to a data storage device 412 and a memory 410. Processor 404 controls the overall operation of computer 402 by executing computer program instructions that define such operations. The computer program instructions may be stored in data storage device 412, or other computer readable medium, and loaded into memory 410 when execution of the computer program instructions is desired. Thus, the method and workflow steps or functions of FIG. 1 can be defined by the computer program instructions stored in memory 410 and/or data storage device 412 and controlled by processor 404 executing the computer program instructions. For example, the computer program instructions can be implemented as computer executable code programmed by one skilled in the art to perform the method and workflow steps or functions of FIG. 1. Accordingly, by executing the computer program instructions, the processor 404 executes the method and workflow steps or functions of FIG. 1. Computer 402 may also include one or more network interfaces 406 for communicating with other devices via a network. Computer 402 may also include one or more input/output devices 408 that enable user interaction with computer 402 (e.g., display, keyboard, mouse, speakers, buttons, etc.).

Processor 404 may include both general and special purpose microprocessors, and may be the sole processor or one of multiple processors of computer 402. Processor 404 may include one or more central processing units (CPUs), for example. Processor 404, data storage device 412, and/or memory 410 may include, be supplemented by, or incorporated in, one or more application-specific integrated circuits (ASICs) and/or one or more field programmable gate arrays (FPGAs).

Data storage device 412 and memory 410 each include a tangible non-transitory computer readable storage medium. Data storage device 412, and memory 410, may each include high-speed random access memory, such as dynamic random access memory (DRAM), static random access memory (SRAM), double data rate synchronous dynamic random access memory (DDR RAM), or other random access solid state memory devices, and may include non-volatile memory, such as one or more magnetic disk storage devices such as internal hard disks and removable disks, magneto-optical disk storage devices, optical disk storage devices, flash memory devices, semiconductor memory devices, such as erasable programmable read-only memory (EPROM), electrically erasable programmable read-only memory (EEPROM), compact disc read-only memory (CD-ROM), digital versatile disc read-only memory (DVD-ROM) disks, or other non-volatile solid state storage devices.

Input/output devices 408 may include peripherals, such as a printer, scanner, display screen, etc. For example, input/output devices 408 may include a display device such as a cathode ray tube (CRT) or liquid crystal display (LCD) monitor for displaying information to the user, a keyboard, and a pointing device such as a mouse or a trackball by which the user can provide input to computer 402.

An image acquisition device 414 can be connected to the computer 402 to input image data (e.g., medical images) to the computer 402. It is possible to implement the image acquisition device 414 and the computer 402 as one device. It is also possible that the image acquisition device 414 and the computer 402 communicate wirelessly through a network. In a possible embodiment, the computer 402 can be located remotely with respect to the image acquisition device 414.

Any or all of the systems and apparatus discussed herein, including the machine learning based models (including the deep image-to-image network and the encoder and decoder networks) applied at step 104 of FIG. 1, may be implemented using one or more computers such as computer 402.

One skilled in the art will recognize that an implementation of an actual computer or computer system may have other structures and may contain other components as well, and that FIG. 4 is a high level representation of some of the components of such a computer for illustrative purposes.

The foregoing Detailed Description is to be understood as being in every respect illustrative and exemplary, but not restrictive, and the scope of the invention disclosed herein is not to be determined from the Detailed Description, but rather from the claims as interpreted according to the full breadth permitted by the patent laws. It is to be understood that the embodiments shown and described herein are only illustrative of the principles of the present invention and that various modifications may be implemented by those skilled in the art without departing from the scope and spirit of the invention. Those skilled in the art could implement various other feature combinations without departing from the scope and spirit of the invention.

The invention claimed is:

1. A computer implemented method comprising:
receiving one or more input medical images of a heart of a patient, a voltage map of the heart of the patient, and an activation map of the heart of the patient;
extracting features from the voltage map and the activation map using an encoder network;
generating an ablation map identifying target ablation locations on the heart using one or more trained machine learning based models, wherein the one or more trained machine learning based models receive as input the one or more input medical images, the features extracted from the voltage map, and the features extracted from the activation map and generate the ablation map; and
outputting the ablation map.

2. The computer implemented method of claim 1, further comprising:
generating the voltage map by simulating cardiac electrophysiology of the patient using a patient-specific model of the heart.

3. The computer implemented method of claim 1, wherein the one or more trained machine learning based models are trained using a synthetic training dataset, the synthetic training data generated by:
creating a fiber architecture for each anatomical model of one or more anatomical models;
generating a set of electrical tissue properties for each of the one or more anatomical models;
simulating cardiac electrophysiology over a period of time for the set of electrical tissue properties for a number of stimulations; and
identifying target ablation locations based on the simulating to generate a training ablation map.

4. The computer implemented method of claim 1, wherein generating an ablation map identifying target ablation locations on the heart using one or more trained machine learning based models comprises:
generating the ablation map identifying the target ablation locations on the heart using the one or more trained machine learning based models based on a dose of a drug the patient is on.

5. The computer implemented method of claim 1, wherein the one or more input medical images comprises a plurality of input medical images, and generating an ablation map identifying target ablation locations on the heart using one or more trained machine learning based models comprises:
generating the ablation map identifying the target ablation locations on the heart using the one or more trained machine learning based models based on motion of the patient in a pair of the plurality of input medical images.

6. The computer implemented method of claim 1, further comprising:
performing ablation on the target ablation locations identified in the ablation map.

7. An apparatus comprising:
means for receiving one or more input medical images of a heart of a patient, a voltage map of the heart of the patient, and an activation map of the heart of the patient;
means for extracting features from the voltage map and the activation map using an encoder network;
means for generating an ablation map identifying target ablation locations on the heart using one or more trained machine learning based models, wherein the one or more trained machine learning based models receive as input the one or more input medical images, the features extracted from the voltage map, and the features extracted from the activation map and generate the ablation map; and
means for outputting the ablation map.

8. The apparatus of claim 7, further comprising:
means for generating the voltage map by simulating cardiac electrophysiology of the patient using a patient-specific model of the heart.

9. A non-transitory computer readable medium storing computer program instructions, the computer program instructions when executed by a processor cause the processor to perform operations comprising:
receiving one or more input medical images of a heart of a patient, a voltage map of the heart of the patient, and an activation map of the heart of the patient;
extracting features from the voltage map and the activation map using an encoder network;
generating an ablation map identifying target ablation locations on the heart using one or more trained machine learning based models, wherein the one or more trained machine learning based models receive as input the one or more input medical images, the features extracted from the voltage map, and the features extracted from the activation map and generate the ablation map; and
outputting the ablation map.

10. The non-transitory computer readable medium of claim 9, wherein the one or more trained machine learning based models are trained using a synthetic training dataset, the synthetic training data generated by:
creating a fiber architecture for each anatomical model of one or more anatomical models;
generating a set of electrical tissue properties for each of the one or more anatomical models;
simulating cardiac electrophysiology over a period of time for the set of electrical tissue properties for a number of stimulations; and
identifying target ablation locations based on the simulating to generate a training ablation map.

11. The non-transitory computer readable medium of claim 9, wherein generating an ablation map identifying target ablation locations on the heart using one or more trained machine learning based models comprises:
generating the ablation map identifying the target ablation locations on the heart using the one or more trained machine learning based models based on a dose of a drug the patient is on.

12. The non-transitory computer readable medium of claim 9, wherein the one or more input medical images comprises a plurality of input medical images, and generating an ablation map identifying target ablation locations on the heart using one or more trained machine learning based models comprises:
generating the ablation map identifying the target ablation locations on the heart using the one or more trained machine learning based models based on motion of the patient in a pair of the plurality of input medical images.

* * * * *